United States Patent
Stead et al.

(10) Patent No.: US 6,399,581 B1
(45) Date of Patent: Jun. 4, 2002

(54) COMPOUND POSSESSING POTENT THROMBIN RECEPTOR ANTAGONIST ACTIVITY

(75) Inventors: Paul Stead, Hertfordshire (GB); Amy E. Wright; Shirley A. Pomponi, both of Ft. Pierce, FL (US); David Langley, Hertfordshire (GB)

(73) Assignees: Harbor Branch Oceanographic Institution, Inc., Fort Pierce, FL (US); Glaxo Wellcome Inc. (GB)

( * ) Notice: Subject to any disclaimer, the term of this patent is extended or adjusted under 35 U.S.C. 154(b) by 0 days.

(21) Appl. No.: 09/568,694

(22) Filed: May 11, 2000

Related U.S. Application Data

(60) Provisional application No. 60/133,574, filed on May 11, 1999.

(51) Int. Cl.⁷ .................. A01N 43/04; A16K 31/70; G01N 33/53
(52) U.S. Cl. .................. 514/28; 435/7.1
(58) Field of Search .................. 514/22–30; 536/5, 536/4.1; 435/7.1

(56) References Cited

U.S. PATENT DOCUMENTS 5,023,250 A * 6/1991 Adams et al.

FOREIGN PATENT DOCUMENTS

JP 01163196 of 1988

OTHER PUBLICATIONS

Kobayashi et al., Marine Natural Products. XXVIII. "The Structures of Sarasinosides A1, A2, A3, B1, B2, B3, C1, C2, and C3, 9 New Norlanostane–Triterpenoidal Oligoglycosides from the Puauan Marine Sponge Asteropus Sarasinosum", Chem. Pharm. Bull. 39 1991.*

Carmely et al., "The Structure of Eryloside A, A New Antitumor and Antifungal 4–Methylated Sterodial Glycoside From the Sponge Erylus Lendenfeldi", J. Natural Products, vol. 52, No. 1 pp 167–170, 1989.*

Takei, et al., "mechanism of Inhibition of lgE–Dependent Histamine Release From Rat Mast Cells By Penasterol and Penasterone" J. Pharm. Sci. vol.84 No. 2, Feb. 1995.*

Gulativa et al., "ErylosideE from An Alantic Sponge Erylus goffrilleri" Tetrahedron Lett. vol. 35, No. 25, pp4299–4302, 1994.*

Kobayashi et al.(Marine Natural Products. XXVIII. The Structures of Sarasinosides A1, A2, A3, B1, B2, B3, C1, C2, and C3, nine new Norlanostane–Triterpenoidal Oligoglycosides from the Palauan Marine Sponge Asteropus Sarasinosum, Chem. Pharm. Bull. 39, 1991).*

Carmely et al.("The Structure of Eryloside A, A New Antitumor and Antifungal 4–Methylated Sterodial Glycoside From the Sponge Erylus Lendenfeldi", J. Natural Products, vol. 52, No. 1, pp. 167–170, 1989).*

(List continued on next page.)

Primary Examiner—Kenneth R. Horlick
Assistant Examiner—Christine Maupin
(74) Attorney, Agent, or Firm—Saliwanchik, Lloyd & Saliwanchik

(57) ABSTRACT

The subject invention concerns eryloside F, a novel disaccharide of the steroidal carboxylic acid penasterol. This compound can be isolated from an extract of the marine sponge *Erylus formosus*. The compound is a potent thrombin receptor antagonist and, furthermore, inhibits human platelet aggregation. Longer chain penasterol oligosaccharides were also isolated and characterized but these had weaker activity than eryloside F. The subject invention also concerns methods for inhibiting thrombin receptor activity and methods for inhibiting platelet aggregation through the administration of eryloside F, or a salt, derivative or analog thereof.

4 Claims, 3 Drawing Sheets

OTHER PUBLICATIONS

Takei, M., A. Umeyama, N. Shoji, S. Arihara, K. Endo (1995) "Mechanism of Inhibition of IgE–Dependent Histamine Release from Rat Mast Cells by Penasterol of Penasterone" *Journal of Pharmaceutical Sciences* 84(2):228–230.

D'Auria, M. Valeria, Luigi Gomez Paloma, Luigi Minale, Raffaele Riccio (1992) "Structure Characterization By Two Dimensional NMR Spectroscopy, of Two Marine Triterpene Oligoglycosides From A Pacific Sponge of The Genus Erylus" (1992) *Tetrahedron* 48(3):491–498.

Fujioka, Toshihiro, Masayo Iwamoto, Yukiko Iwase, Hikaru Okabe, Kunihide Mihashi, Tatsuo Yamauchi (1988) "Studies on the Constituents of *Actinostermma lobatum* Maxim. III. Structures of Actinostemmosides E and F, New Baccharane-Type Triterpene Glycosides Isolated from the Herb" *Chem. Pharm. Bull.* 36(8):2772–2777.

Jaspars, Marcel and Phillip Crews (1994) "A Triterpene Tetrasaccharide, Formoside, from the Caribbean Choristida Spone *Erylus Formosus*" *Tetrahedron Letters* 35(41):7501–7504.

Carmely, Shumel, Michal Roll, Yosi Loya, Yoel Kashman (1989) "The Structure Of Eryloside A, A New Antitumor And Antifungal 4–Methylated Steroidal Glycoside From The Sponge *Erylus Lendenfeldi*" (1989) *Journal of Natural Products* 52(1):167–170.

Shoji, Noboru, Akemi Umeyama, Setsuko Motoki, Shigenobu Arhara (1992) "Potent Inhibitors of Histamine Release, Two Novel Triterpendoids From the Okinawan Marine Sponge *Penares Incrustans*" *Journal of Natural Products* 55(1):1682–1685.

Cheng, Jie–fei et al. (1988) "Penasterol, a Novel Antileukemic Sterol from the Okinawan Marine Sponge Penares sp." *J. Chem. Soc. Perkin Trans.* I 8:2403–2406.

Gulavita, Nanda K., Amy E. Wright, Michelle KellyBorges, Ross E. Longley (1994) "Eryloside E From An Atlantic Sponge *Erylus goffrilleri*" *Tetrahedron Letters* 35(25):4299–4302.

Bewley, Carole A., Cécile Debitus, D. John Faulkner (1994) "Microscleroderma A and B. Antifungal Cyclic Peptides from the Lithisid Sponge Microscleroderma sp." *J. Am. Chem. Soc.* 116:7631–7636.

Schmidt, Eric W. and D. John Faulkner (1998) "Microsclerodermins C–E, Antifungal Cyclic Peptides from the Lithistid Marine Sponges *Theonella sp.*and *Microscleroderma sp.*" (1998) *Tetrahedron* 54:3043–3056.

* cited by examiner

COMPOUND POSSESSING POTENT THROMBIN RECEPTOR ANTAGONIST ACTIVITY

CROSS-REFERENCE TO A RELATED APPLICATION

This application claims the benefit of U.S. Provisional Application No. 60/133,574, filed May 11, 1999.

BACKGROUND OF THE INVENTION

Penasterol (1, FIG. 1), an acidic steroidal metabolite closely related to lanosterol (2, FIG. 1) and possessing potent antileukemic activity, was originally isolated from Penares sp. by Cheng et al in 1988 (Cheng, J.F., J. Kobayashi, H. Nakamura, Y. Ohizumi, Y. Hirata, and T. Sasaki [1988] *J. Chem. Soc. Perkin Trans.I* 8:2403–2406; Kobayashi, J. and Y. Ooizurni, [1988] JP 01163196 A2 890627). The compound, together with its close analogues penasterone and acetylpenasterol, isolated from *Penares incrustans*, have been shown to inhibit IgE-dependent histamine release from rat mast cells (Shoji, N., A. Umeyama, S. Motoki, S. Arihara, T. Ishida, K Nomoto, J. Kobayashi, M. Takei [1992] *J. Nat. Prod.* 55(11):1682–1685; Takei, M., A. Umeyama,N. Shoji, S. Arihara, K. Endo [1995] *J. Pharm. Sci.* 84(2):228–230). The erylosides (Carmely, Y., M. Roll, Y. Loya, Y. Kashman [1989] *J. Nat. Prod.* 52(1):167–170; D'auria, M. V., Paloma L. Gomez, R. Riccio, C. Debitus [1992] *Tetrahedron Lett* 48(3):491–498; Gulavita, N. K., A. E. Wright, M. Kelly-Borges, R. E. Longley [1994] *Tetrahedron Lett* 35(25):4299–4302), isolated from various Erylus spp. constitute a family of glycosides of penasterol and related aglycones. Eryloside A possesses antitumor and antifungal activity, while Eryloside E is an antagonist of C5 a-receptorbinding. The penasterol tetrasaccharide formoside (Jaspars, M. and P. Crews [1994] *Tetrahedron Lett.* 35(41):75,01–7504) was recently isolated by Jaspars et al. from *Erylus formosus*.

BRIEF SUMMARY OF THE INVENTION

The subject invention pertains to a novel penasterol disaccharide, eryloside F (3, FIG. 1). Eryloside F has potent thrombin receptor antagonist activity and, furthermore, inhibits platelet aggregation. Advantageously, the compound has low toxicity against liver hepatocyte (HepG2) cells. The subject invention further concerns the use of salts, derivatives, and analogs of eryloside F. Such salts, derivatives, and analogs of eryloside F can be prepared by a person skilled in the art having the benefit of the disclosure provided herein.

DETAILED DESCRIPTION OF THE INVENTION

Eryloside F is a novel steroidal disaccharide metabolite of *Erylus formosus* which possesses potent and relatively selective thrombin receptor antagonist activity. As discussed below, activity of this compound in the calcium mobilization fluorescence imaging plate reader (FLIPR) assay was found to be predictive of functional activity in a platelet aggregation assay. Longer chain penasterol oligosaccharides were also isolated and characterized but these had weaker activity than eryloside F. The subject invention further concerns the use of salts, derivatives, and analogs of eryloside F. Such salts, derivatives, and analogs of eryloside F can be prepared by a person skilled in the art having the benefit of the disclosure provided herein. Eryloside F, and the salts, derivatives and analogs thereof, can also be prepared in pharmaceutical compositions with a physiologically acceptable carrier or diluent.

The present invention also concerns methods for inhibiting thrombin receptor activity using eryloside F, or a salt, derivative or analog thereof. Eryloside F compounds of the invention can also be used to inhibit platelet aggregation. In one embodiment, an effective amount of compound is administered to an animal in need of such treatment. Preferably, the animal is a human or other mammal.

The compounds of the. invention are useful in treating thrombotic—and platelet aggregation-related disorders and conditions, such as arterial and venous thrombosis, acute myocardial infarction, stroke, reocclusion following thrombolytic therapy and angioplasty, arteriosclerosis, unstable angina, abrupt closure, restenosis following angioplasty, inflammation, metastasis and wound healing.

Figure 2:
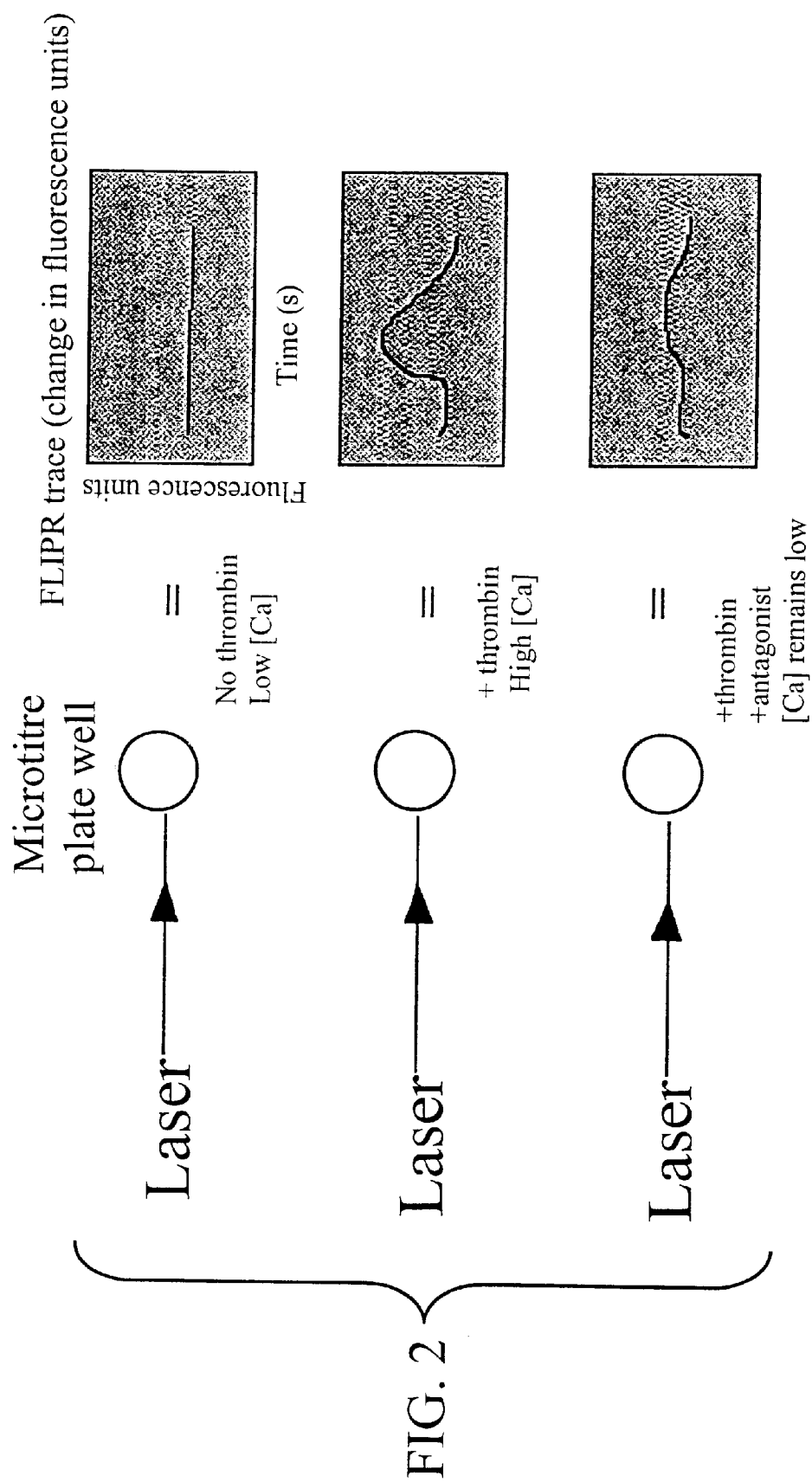
FIG. 2 shows an FLIPR based assay for detection of thrombin receptor antagonists.

Tests were conducted of inhibition of thrombin-induced calcium mobilization in HeLa cells (see FIG. 2). Two highly active marine samples—both extracts of *Erylus formosus*—were fractionated by HPLC, using the calcium mobilization assay to guide the fractionations. The HPLC profiles of the extracts were very similar, and in both cases the biological activity resided in the same chromatographic fractions indicating common active principles. One of these was fully deconvoluted, and several active components were isolated. These were all glycosides of penasterol though differing in the number of sugar residues attached at the C-1 position. Interestingly, biological activity varied inversely with the length of the oligosaccharide chain; the disaccharide eryloside F which was the shortest chain oligosaccharide isolated from the active extract showed the most potent activity, and so its chemical structure was fully elucidated.

Modifications of the compounds disclosed herein can readily be made by those skilled in the art. Thus, analogs, derivatives, and salts of the exemplified compounds are within the scope of the subject invention. With a knowledge of the compounds of the subject invention, and their structures, skilled chemists can use known procedures to synthesize these compounds from available substrates.

As used in this application, the terms "analogs" and "derivatives" refer to compounds which are substantially the same as another compound but which may have been modified by, for example, adding additional side groups. The terms "analogs" and "derivatives" as used in this application also may refer to compounds which are substantially the same as another compound but which have atomic or molecular substitutions at certain locations in the compound.

Analogs or derivatives of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl, $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

All patents, patent applications, provisional applications, and publications referred to or cited herein are incorporated by reference in their entirety to the extent they are not inconsistent with the explicit teachings of this specification.

Materials and Methods

Recording of nmr and ms data: NMR spectra were recorded on a Varian INOVA-750 spectrometer, with $^1$H observation at 750 MHz, using a 5 mm inverse $^1$H/$^{13}$C/$^{15}$N triple probe fitted with az gradient coil. All data were acquired using pulse sequences supplied by Varian Instruments Ltd. These included 1 D-TOCSY, DQFCOSY, HMQC, and gradient-assisted HMBC.

The 1D-TOCSY spectra were acquired using an eburp excitation pulse over 50 Hz and a mix time of 120 milliseconds. Typically 64 transients were acquired into 96K data points over a spectral width of 20 ppm and a pulse repetition time of 3.4 seconds. The DQFCOSY spectrum was acquired using 512 increments of 16 transients. FIDs were collected into 2K data points with a spectral width of 4.4 KHz and a pulse repetition time of 1.3 seconds. The HMQC spectrum was acquired using 256 increments of 32 transients. FIDs were collected into 1K data points with a spectral width of 4.4 KHz and a pulse repetition time of 0.6 seconds. The gradient assisted HMBC spectrum was acquired using 256 increments of 96 transients. FIDS were collected into 2K data points with a spectral width of 40 KHz and a pulse repetition time of 1.8 seconds.

Mass spectra were measured on a Finnigan Mat LCQ ion trap mass spectrometer, fitted with an electrospray interface, operated in both positive and negative ionization modes.

Collection of Specimens: Two samples. of the sponge *Erylus formosus* Sollas, 1886 [Class, Demospongiae, Order Choristida, Family Geodiidae], were analyzed in this study. The first specimen (HBOI #5-VI-86-4-013) was collected by scuba at a depth of 60 feet in the Bahamas off Black Rock in the Little Bahama Bank (latitude 26 15.3° N., longitude 79 39.3° W.). The second specimen (HBOI #16-XI-87-2-019) was collected by scuba at a depth of 55 feet in the Bahamas at Wood Cay, northwest of Grand Bahama Island (latitude 26 44.5° N., longitude 79 01.5° W.). Both specimens are described as growing in a thick encrusting form with a smooth thin ectosome and very small pores distributed over the surface. The exterior of the sponge is black while the interior is tan in color. All features of the sponge conform to the taxonomic assignment of *Erylus formosus* as described in Wiedenmeyer (Wiedenmeyer, F. [1977] "Shallow Water Sponges of the Western Bahamas" Experientia Supplementum28, Birkhauser, Verlag, Basel, p. 181). Voucher specimens have been deposited at the Harbor Branch Oceanographic Museum with catalog acquisition numbers of 003:00937 and 003:00938, respectively.

Preparation of extracts of *Erylus formosus* and isolation of eryloside F: To generate samples for screening, extracts were prepared by grinding 8 g of frozen sponge with ethanol (20 ml). After standing for 24 hours at −20° C., solid material was removed by filtration. The filtrate was dried, and a proportion was dissolved in DMSO to give a 5 mg/ml solution. After detection of activity, a larger proportion was dissolved in DMSO to give a 5 mg/ml solution. After detection of activity, a larger extract was prepared for sample HBOI# 5-VI-86-4-013. Seventy five (75) g of the frozen sponge was extracted exhaustively with ethanol using a Waring blender. The extract was filtered and the solvent removed by distillation under reduced pressure to yield 3.5 g of a crude ethanol extract. A portion of this extract (350 mg) was taken and dissolved in aqueous buffer (100 mM ammonium dihydrogen phosphate in water, pH 2.5–20 ml) then chromatographed using preparative HPLC as follows: column kromasil 7 μm C8 15 cm×2 cm. Mobile phase 50% v/v acetonitrile, 50 mM $NH_4H_2PO_4$ in water with 3 ml/L $H_3PO_4$ added. Flow rate 20 ml/min. Injection volume 5 ml. Eryloside F eluted after 30 min approximately. Relevant fractions were pooled and acetonitrile was removed by rotary evaporation. The aqueous solution was de-salted by adsorption onto C 18 silica (500 mg Bond-Elut cartridge, Varian Ltd.), resin washed with water than adsorbed material eluate with methanol (2 ml). The eluate was concentrated to dryness using a Speedivac concentrator to yield eryloside F (2.0 mg) as a white solid.

Thrombin receptor antagonist assay using FLIPR (fluorescence)imaging plate reader: HeLa cells were suspended in complete media and the cell density measured then adjusted to give a final cell density of $2.0\times10^5$/ml. 100 μl of cell suspension was dispensed into 96-well microtitre plates using a Multipdrop 96/384 well plate dispenser. Plates were incubated overnight at 37° C./5% $CO_2$, 100 μl of a solution of fluo-3 (Cambridge Biosciences, UK) was added to all wells giving 10 μg/ml final concentration. The plates were then placed in a tissue culture incubator in stacks of no more than three high. Test samples (in DMSO) were added to wells (to give 1% v/v final DMSO concentration) followed by thrombin (final concentration 0.3 U/ml), then plates placed on the FLIPR. Fluorescence output was read every 1 second for the first 20 seconds then every 5 seconds for a further 30 seconds.

Platelet aggregation assay: Blood was withdrawn from the antecubal vein of healthy human volunteers who had taken no medication for 14 days. The blood (9 volumes) was anti-coagulated with 1 volume of 3.8% w/v tri-sodium citrate, to give a final citrate concentration of 12.9 mM. To each 20 ml volume of anti-coagulated blood 50 μl of a 10 μg/ml prostacyclin ($PGI_2$) solution was added to prevent activation during the platelet isolation process. The prostacyclin-treated blood was then centrifuged (1280×g; 4 minutes) to yield platelet-rich plasma (PRP). The PRP was carefully removed from above the red and white blood cells with a plastic Pasteur pipette and transferred to a clean Sterilin® (30 ml) tube. This PRP was then centrifuged (1280×g; 10 minutes) to pellet the platelets. The supernatant (platelet-poor plasma) was discarded and the platelets resuspended in a Hepes buffer (NaCl (8 g/l); $NaHCO_3$ (1 g/l); KCl (0.2 g/l); $KH_2PO_4$ (0.1 g/l); Hepes (1.2 g/l); D-Glucose (1 g/l) adjusted to a pH of 6.4. The resultant platelet suspension was again centrifuged (1280×g; 8 minutes) to pellet the platelets. The supernatant was discarded and the platelets resuspended in a Hepes buffer of the same composition but adjusted to a pH of 7.4. The platelet count was then adjusted to 300,000 platelets/μl, following quantification on a Sysmex K1000 Haematological analyser and $CaCl_2$ (1 mM) and $MgCl_2$ (0.5 mM) were added back. The platelet preparation was then left for at least 30 minutes before aggregation studies were performed.

Following are examples which illustrate procedures for practicing the invention. These examples should not be construed as limiting. All percentages are by weight and all solvent mixture proportions are by volume unless otherwise noted.

EXAMPLE 1

Structure Determination

The structure of eryloside F was determined using a combination of MS and 1D-and 2D-NMR data. The observations of positive ions at m/z 768 $[M+NH_4]^+$ and 1518 $[dimer+NH_4]^+$ and negative ions at m/z 749 $[M-H]^-$ and 1499 $[dimer-H]^-$ were consistent with a molecular weight of 750 amu. Initial examination of the 1D proton and one bond $^1$H-$^{13}$C correlation NMR data suggested the presence of two sugars (anomeric signals at $\delta^1H$ 4.55→$\delta^{13}C$ 104.9 and $\delta^1H$ 4.47 →$\delta^{13}C$ 105.6). This was supported by fragment ions in the positive ion mass spectrum which were consistent with the loss of a C6 sugar (m/z 589 $[M+NH_4\text{-sugar}]^+$, 571 $[M+H\text{-sugar}]^-$) and with the loss of both a C6 and a C5 sugar (m/z 457 $[M+NH_4\text{-2 sugars}]+$).

Careful analysis of the $^1H$-$^1H$, one bond and long range $^1H$-$^{13}C$ correlation data served to identify the aglycone part of the molecule as penasterol. The observed chemical shifts (Table 1) for the aglycone are in good agreement with those reported for the closely related penasterol glycoside, formoside.

TABLE 1

$^{13}C$ (188.6 MHz) and $^1H$ (750 MHz) NMR data in $CD_3OD$ for eryloside F.

| $\delta^{13}C^a$ | | $\delta^1H^b$ | $\delta^{13}C$ | | $\delta^1H$ |
|---|---|---|---|---|---|
| 36.1 | 1 | 1.78; 1.29 | 125.7 | 24 | 5.09 (m) |
| 27.2 | 2 | 1.91; 1.74 | 131.6 | 25 | — |
| 90.3 | 3 | 3.14 (dd, 12.0, 4.5) | 17.3 | 26 | 1.60 (brs) |
| 40.1 | 4 | — | 25.5 | 27 | 1.67 (brs) |
| 51.3 | 5 | 1.12 (dd; 12.5, 2) | 179.6 | 28 | — |
| 18.9 | 6 | 1.71; 1.54 | 28.0 | 29 | 1.04 (s) |
| 28.3 | 7 | 2.11; 1.97 | 16.4 | 30 | 0.88 (s) |
| 128.6 | 8 | — | | | |
| 140.7 | 9 | — | | Ara | |
| 38.2 | 10 | — | 104.9 | 1' | 4.55 (d, 5.5) |
| 22.9 | 11 | 2.18 (m); 2.11 | 79.7 | 2' | 3.86 (dd, 7.5, 5.5) |
| 32.3 | 12 | 2.23 (m); 1.71 | 72.8 | 3' | 3.78 (dd, 7.5, 3.5) |
| 47.6 | 13 | — | 68.1 | 4' | 3.87 (m) |
| 63.6 | 14 | — | 64.2 | 5' | 3.84 (dd, 11.5, 5.0) |
| | | | | | 3.51 (dd, 11.5, 2.0) |
| 28.4 | 15 | 2.08; 1.59 | | | |
| 29.9 | 16 | 2.07; 1.39 | | Gal | |
| 51.7 | 17 | 1.54 | 105.6 | 1' | 4.47(d, 7.5) |
| 17.9 | 18 | 0.80 (s) | 73.1 | 2' | 3.56 (dd, 9.5, 7.5) |
| 19.6 | 19 | 1.06 (s) | 74.6 | 3' | 3.48 (dd, 9.5, 3.5) |
| 36.6 | 20 | 1.45 | 69.6 | 4' | 3.86 (dd, 3.0, 1.0) |
| 18.7 | 21 | 0.94 (d, 6.5) | 76.4 | 5' | 3.49 (td, 6.5, 1.0) |
| 36.9 | 22 | 1.43; 1.04 | 61.6 | 6' | 3.71 (d, 6.5) |
| 25.4 | 23 | 2.02; 1.88 | | | |

[a]Referenced to residual $CHD_2OD$ at 48.9 ppm.
[b]Referenced to residual $CHD_2OD$ at 3.31 ppm. Multiplicities and coupling constants (±0.5 Hz) are given in parentheses.

The linking points between the sugars and the aglycone followed from the long range $^1H$-$^{13}C$ correlations ($\delta^1H$ 4.55 → $\delta$—C 90.3 and $\delta^1H$ 4.47 → $\delta^{13}C$ 79.7) observed from the anomeric protons.

TABLE 2

Key Long-Range $^1H$ → $^{13}C$ correlations for eryloside F

| $\delta^1H$ | $\delta^{13}C$ |
|---|---|
| 0.80 | 32.3; 47.6; 51.7; 63.6 |
| 0.88 | 28.0; 40.1; 51.3; 90.3 |
| 0.94 | 36.6; 36.9; 51.7 |
| 1.04 | 16.4; 40.1; 51.3; 90.3 |
| 1.06 | 36.1; 38.2; 51.3; 140.7 |
| 1.59 | 179.6 |
| 1.60 | 25.5; 125.7; 131.6 |
| 1.67 | 17.3; 125.7; 131.6 |
| 2.08 | 179.6 |
| 4.47 | 79.7 |
| 4.55 | 90.3 |

Figure 1:
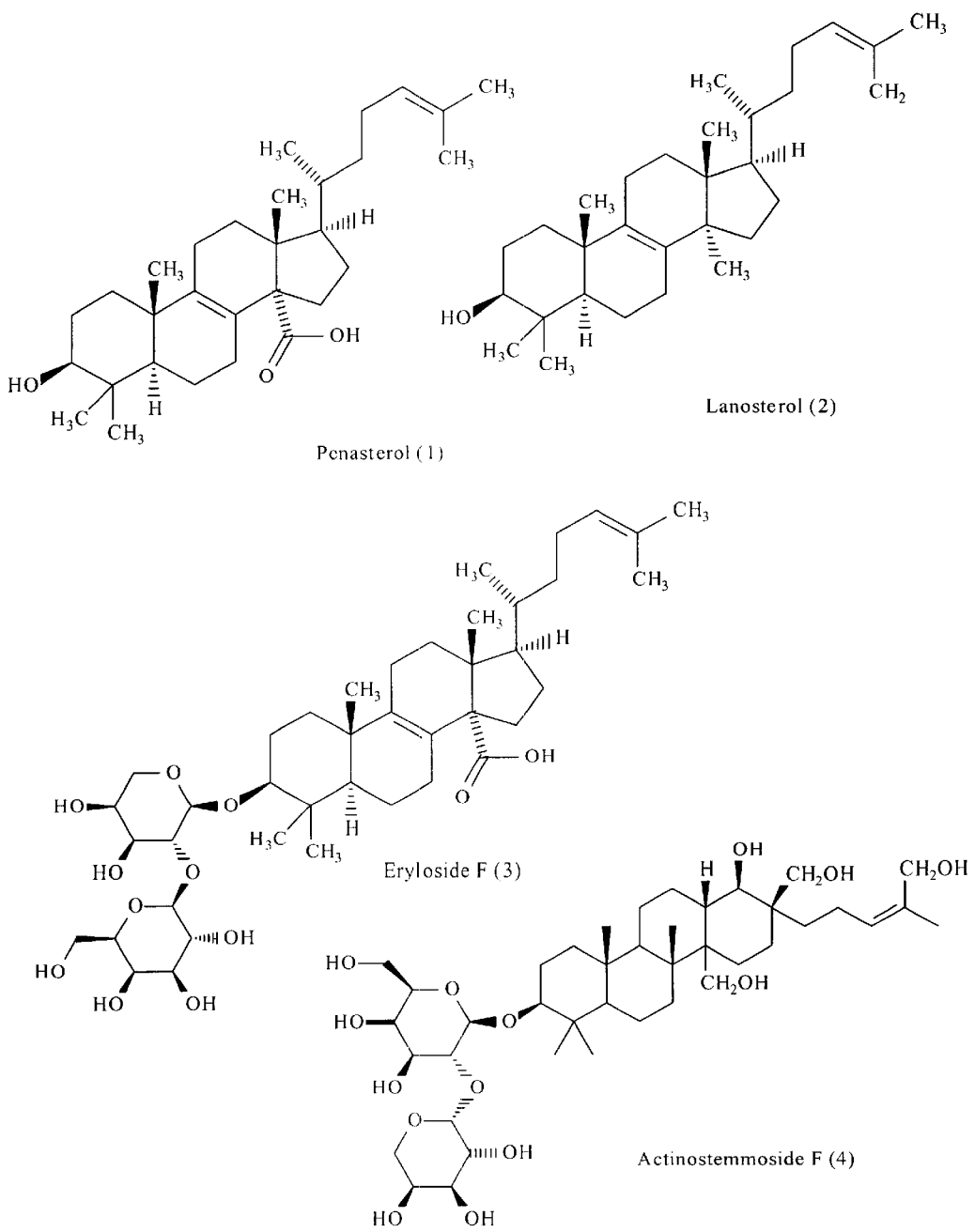
FIG. 1 shows the structure of penasterol, lanosterol; eryloside F, and actinostemmoside F.

The stereochemistry of the sugars was identified from an analysis of the $^1H$-$^1H$ coupling constants (Table 1). These are very similar to those previously observed from this disaccharide group in actinostemmoside F (Fujioka, Tr., M. Iwamoto, Y. lwase, H. Okabe, K. Mihasi, T. Yamauchi [1988] *Chem. Pharm. Bull.* 36:2772–2777) (see FIG. 1). The measurement of these couplings was facilitated by the acquisition of selective 1D-TOCSY spectra starting from each anomeric proton.

EXAMPLE 2
Biological Profiling of Eryloside F

An assay was conducted based upon measurement of thrombin-induced intracellular calcium mobilization in HeLa cells, which constitutively express the thrombin receptor. Intracellular calcium flux was measured using the fluorescent dye fluo-3' which in the absence of calcium ions fluoresces only weakly, but in the presence of calcium increases fluorescence by approximately 100-fold. Fluorescence was measured using a fluorescence imaging plate reader (FLIPR; see FIG. 2).

Compounds which showed activity inhibiting thrombin-induced calcium mobilization were tested in a platelet aggregation assay. Platelet aggregation, in a human washed platelet preparation, was quantified using an optical aggregometer. This measures an increase in light transmission as platelet aggregation leads to less light being blocked. A washed platelet preparation was used because it is free of plasma fibrinogen, allowing thrombin to be used without the complication of the sample clotting. Platelets were isolated from citrated whole blood by a series of centrifugation steps and resuspended in a physiological Hepes buffer. The compounds were tested against thrombin, SFLLRN (a thrombin receptor activating peptide) and U-46619 (a stable thromboxane A2 mimetic) in order to determine if they were selective at inhibiting protease-activated receptor 1 (PAR-1) mediated platelet aggregation (see FIG. 3).

Figure 3:
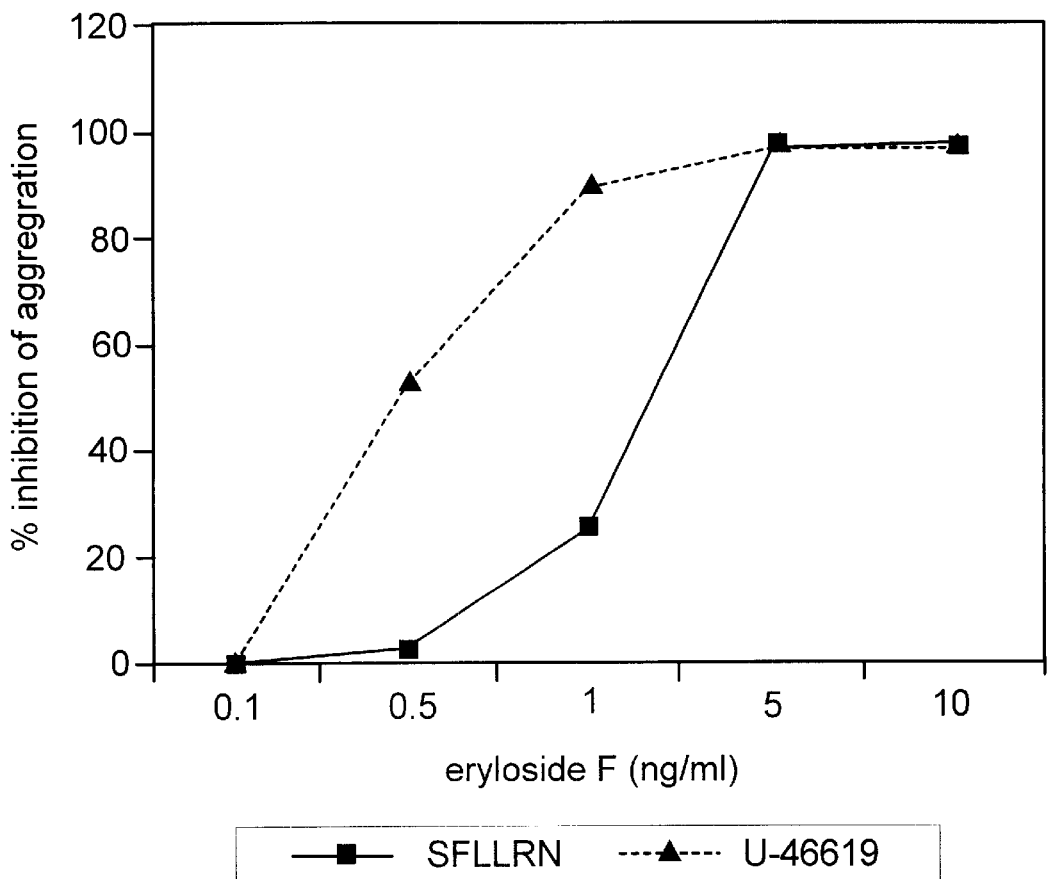
FIG. 3 shows inhibition of platelet aggregation induced by SFLLRN (3 $\mu$M) or U-46619 by eryloside F.

Eryloside F inhibited both SFLLRN(3 $\mu$M)-and U-46619(3 $\mu$M)-induced platelet aggregation in a concentration related manner (FIG. 3). Eryloside F was approximately 6-fold more potent against SFLLRN than against U-46619-induced platelet aggregation, producing $IC_{50}$ values of 0.3 $\mu$g/ml and 1.7 $\mu$g/ml, respectively. Eryloside F was also tested against thrombin (0.1 U/ml)-induced platelet aggregation, however its inhibitory potency relative to that against SFFLRN-induced platelet aggregation was approximately 20-fold lower. Although both SFLLRN and thrombin can activate the same receptor (PAR-1), the mechanism of activation is different. SFLLRN binds to the "active site" of the receptor, while thrombin enzymatically cleaves the N-terminus of the receptor to expose a new N-terminus with the terminal sequence SFLLRN (a tethered ligand), which binds to the active site of the receptor. Eryloside F is probably a weaker antagonist of thrombin-induced platelet aggregation, since it is at a competitive disadvantage relative to the endogenous tethered ligand.

EXAMPLE 3
Formulation and Administration

The compounds of the invention are useful for various non-therapeutic and therapeutic purposes. It is apparent from the testing that the compounds of the invention are effective thrombin receptor antagonists.

Therapeutic application of the new compounds and compositions containing them can be contemplated to be accomplished by any suitable therapeutic method and technique presently or prospectively known to those skilled in the art. Further the compounds of the invention have use as starting material for intermediates for the preparation of other useful compounds and compositions.

The dosage administration to a host in the above indications will be dependent upon the identity of the pathology, the type of host involved, its age, weight, health, kind of concurrent treatment, if any, frequency of treatment and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be. used by persons of ordinary skill in the art. In addition, the pharmaceutical composition can comprise one or more of eryloside compounds as a first active ingredient plus a second active ingredient known in the art. The most effective mode of administration and dosage regimen will depend upon the type of condition to be treated, the severity and course of that condition, previous therapy, the patient's health status, and the judgment of the treating physician. The compositions of the subject invention may be administered to the patient at one time or over a series of treatments. Conventional modes of administration and standard dosage regimens may be used (see Gilman, A. G. et. al. [eds] *The Pharmacological Basis of Therapeutics*, pp. 697–713, 1482, 1489–1491 [1980]; Physicians Desk Reference, 1985 Edition).

The compounds used in these therapies can also be in a variety of forms. These include for example, solid, semi-solid and liquid dosage forms, such as tablets, pills, powders, liquid solutions or suspensions, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch and equivalent carriers and diluents. While effective amounts may vary, as conditions in which compositions are used vary, a minimal dosage required for activity is generally between 0.01 and 100 μg of the compound. To provide for the administration of such dosages for the desired therapeutic treatment, new pharmaceutical compositions of the invention will advantageously comprise between about 0.1% and 45%, and especially, 1 and 15% by weight of the total of one or more of the new compounds based on the weight of the total composition including carrier or diluent.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. Isolated eryloside F having the following formula:

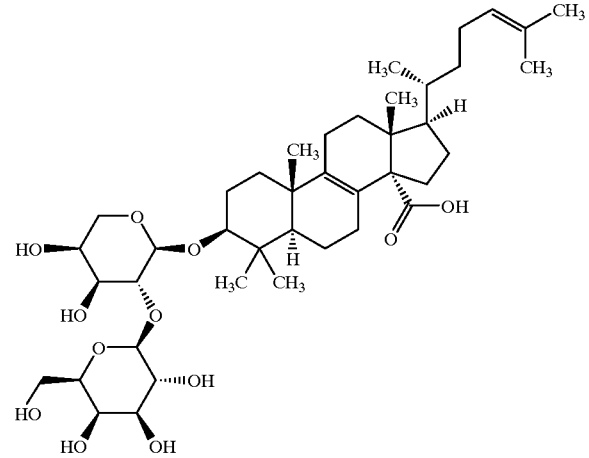

or a salt thereof.

2. The eryloside F according to claim 1, wherein said eryloside F has the spectral data reported in Table 1.

3. A pharmaceutical composition comprising eryloside F, or a salt thereof, with a physiologically acceptable carrier or dilutent, wherein eryloside F has the following formula:

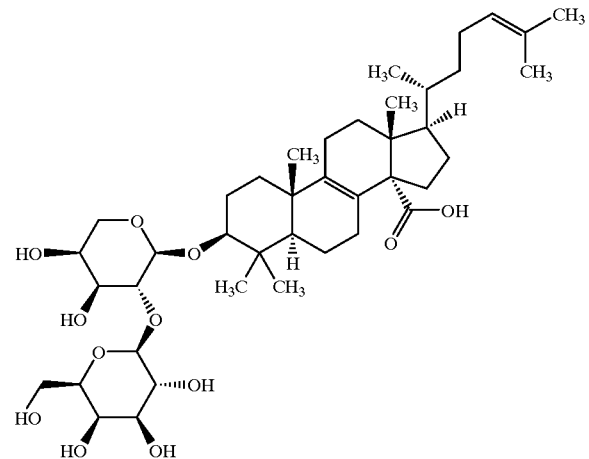

4. The composition according to claim 3, wherein said eryloside F has the spectral data reported in Table 1.

* * * * *

UNITED STATES PATENT AND TRADEMARK OFFICE
CERTIFICATE OF CORRECTION

PATENT NO.      : 6,399,512 B1                                                     Page 1 of 1
DATED           : June 4, 2002
INVENTOR(S)     : Blosse et al.

It is certified that error appears in the above-identified patent and that said Letters Patent is hereby corrected as shown below:

<u>Title page,</u>
Item [75], should read:

-- [75] Inventors:   Alan Blosse, Belmont; Sanjay Thekdi,
                     Santa Clara; Jianmin Qiao, Fremont;
                     Yitzhak Gilboa, Sunnyvale, all of CA
                     (US) --

Signed and Sealed this

Twenty-eighth Day of January, 2003

JAMES E. ROGAN
*Director of the United States Patent and Trademark Office*